United States Patent
Lake et al.

(10) Patent No.: US 10,894,034 B2
(45) Date of Patent: Jan. 19, 2021

(54) ANTI-NEOPLASTIC COMPOUNDS AND METHODS TARGETING QSOX1

(71) Applicants: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US)

(72) Inventors: Douglas Lake, Scottsdale, AZ (US); Erik Castle, Phoenix, AZ (US); Paul Hanavan, Tempe, AZ (US); Douglas Faigel, Scottsdale, AZ (US); Thai Ho, Scottsdale, AZ (US)

(73) Assignees: Arizona Board of Regents on behalf of Arizona State University, Scottsdale, AZ (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/748,784

(22) PCT Filed: Sep. 13, 2016

(86) PCT No.: PCT/US2016/051519
§ 371 (c)(1),
(2) Date: Jan. 30, 2018

(87) PCT Pub. No.: WO2017/048712
PCT Pub. Date: Mar. 23, 2017

(65) Prior Publication Data
US 2019/0008829 A1    Jan. 10, 2019

Related U.S. Application Data (60) Provisional application No. 62/218,732, filed on Sep. 15, 2015.

(51) Int. Cl.
*A61K 31/402* (2006.01)
*A61P 35/00* (2006.01)

(52) U.S. Cl.
CPC ............ *A61K 31/402* (2013.01); *A61P 35/00* (2018.01)

(58) Field of Classification Search
CPC ...... A61K 31/165; A61K 31/60; A61K 45/06; A61K 9/2009; A61K 9/2013; A61K 9/2018; A61K 9/2054; A61K 9/2059; A61K 9/2063; A61K 9/2095; A61K 31/402; A61P 35/00
USPC .................................................. 514/275, 708
See application file for complete search history.

(56) References Cited

U.S. PATENT DOCUMENTS

| | | | |
|---|---|---|---|
| 8,911,959 B2 * | 12/2014 | Lake | G01N 33/68 424/274.1 |
| 8,946,186 B2 | 2/2015 | Lake et al. | |
| 9,546,370 B2 * | 1/2017 | Lake | A61K 39/39558 |
| 2013/0158035 A1 * | 6/2013 | Hansen | A61K 31/4741 514/237.5 |
| 2015/0110786 A1 | 4/2015 | Fass et al. | |
| 2019/0008829 A1 * | 1/2019 | Lake | A61P 35/00 |

OTHER PUBLICATIONS

Gene Transfer and Expression Protocols, pp. 109-128, ed. E. J. Murray, The Humana Press Inc., Clifton, N.J.
National Center for Biotechnology Information. PubChem Compound Database; Cid=1121741, https://pubchem.ncbi.nlm.nih.gov/compound/1121741 (accessed Mar. 7, 2019), 12 pages.
Hanavan et al. "Small Molecule Inhibition of Quiescin Sulfhydryl Oxidase 1 (QSOX1), a Dynamic Pro-Tumorigenic Regulator of the Extracllular Matrix" Arizona State University, Dec. 2015, 1-92.
GenBank Accession No. NP_001004128.1, "sulfhydryl oxidase 1 isoform b precursor [*Homo sapiens*]"Apr. 26, 2017.
GenBank Accession No. NP_002817.2, "sulfhydryl oxidase 1 isoform a precursor [*Homo sapiens*]," May 13, 2017, 3 pages.

* cited by examiner

*Primary Examiner* — Sabiha N Qazi
(74) *Attorney, Agent, or Firm* — Fish & Richardson P.C.

(57) ABSTRACT

Compounds and methods involving inhibition of the enzymatic activity of QSOX1 (FIG. 13). The compounds and methods can be used in treatment of neoplastic cells, for example, to suppress tumor growth and invasion in a variety of cancers, including but not limited to myeloma and cancers of the breast, kidney, and pancreas.

6 Claims, 15 Drawing Sheets

• SBI-0143183 (50,000 compound library)

ANTI-NEOPLASTIC COMPOUNDS AND METHODS TARGETING QSOX1

CROSS-REFERENCE TO RELATED APPLICATIONS

This application represents the U.S. National Stage entry of International Application No. PCT/US2016/051519, filed on Sep. 13, 2016, and claims priority to and the benefit of U.S. Provisional Application No. 62/218,732, filed on Sep. 15, 2015, the disclosures of which are incorporated herein by reference.

FIELD OF THE INVENTION

This disclosure relates to the field of anti-neoplastic compounds and methods and more particularly to such compounds and methods relating to QSOX1 and its gene products.

BACKGROUND OF THE INVENTION

Cancer (and other hyperproliferative diseases) is characterized by uncontrolled cell proliferation. Researchers have explored cancer treatment approaches that inhibit various proteins involved in uncontrolled signal transduction. What remains needed, however, are additional and improved inhibitors of regulatory proteins.

SUMMARY OF THE INVENTION

Quiescin sulfhydryl oxidase 1 (QSOX1) is an enzyme that is over-expressed in many tumor types. Two transcript variants encoding two different isoforms of QSOX1 been found. Recombinant QSOX1 has been expressed and used to screen a library of chemical compounds to identify any compounds that inhibit the enzymatic activity of QSOX1.

In one aspect, this disclosure relates to a compound derived from a chemical library in the Sanford Burnham collection of compounds, 3-methoxy-N-[4-(1-pyrrolidinyl) phenyl]benzamide:

SBI-0143183 or SBI-183 for short

In an additional aspect, this disclosure relates to stereoisomers, prodrugs and pharmaceutically acceptable salts of SBI-183.

In another aspect, this disclosure relates to the use of SBI-183 and related compounds to inhibit QSOX1.

In a further aspect, this disclosure relates to the use of SBI-183 and related compounds to inhibit growth and invasive properties of neoplastic cells.

In still another aspect, this disclosure relates to the use of SBI-183 and related compounds to inhibit neoplastic cells that over-express the QSOX1 enzyme, such as in, for example, myeloma and pancreatic, renal, and breast cancer.

A compound of the present disclosure or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

These and other aspects will be apparent upon reference to the following detailed description and figures. To that end, any patent and other documents cited herein are hereby incorporated by reference in their entirety.

BRIEF DESCRIPTION OF THE DRAWINGS

FIG. 2. QSOX1 is over-expressed in multiple human cancers, but not or minimal in non-malignant tissues. Western blot showing QSOX1 expression in several tumor types. QSOX1-S and -L are short and long variants, respectively. Yellow arrows depict Epstein Barr Virus-transformed B cells from a healthy donor (ND 111) and non-transformed lymphocytes from ND111. MCF-10A is a non-malignant breast cell line. 4T1, 3LL and B16-F10 are murine breast, lung and melanoma tumor cell lines, respectively. Other tumor cell lines are as follows: V18I: Vaginal epithelial cell line; 3ECI: Ectocervical epithelial cell line; A2: Endocervical epithelial cell line; sA2: Endocervical epithelial cell line (daughter of A2 above); CaCo: Colonic adenocarcinoma cell line; HEC-1A: Uterine epithelial cell line; INT 407: Embryonic small intestinal epithelial cell line in ATCC.

DETAILED DESCRIPTION OF THE INVENTION

As used herein, "QSOX1" is Quiescin Sulfhydryl Oxidase 1, also called QSCN6. The protein accession number for the long variant of QSOX1 on the NCBI database is NP_002817, and the accession number for the short form is NP_001004128. As used herein, "QSOX1" refers to both the long and short variants of QSOX1.

In screening for inhibitors, recombinant QSOX1 was produced and tested in fluorogenic assays to make sure it was active. The recombinant enzyme then was sent to the Sanford Burnham Institute for use in the same/similar assay to screen libraries for chemical compounds that inhibit the enzymatic activity of QSOX1.

In one embodiment, a compound derived from a chemical library in the Sanford Burnham collection of compounds, 3-methoxy-N-[4-(1-pyrrolidinyl)phenyl]benzamide was discovered to be an inhibitor (designated SBI-0143183 or SBI-183 for short) of QSOX1.

Figure 1:
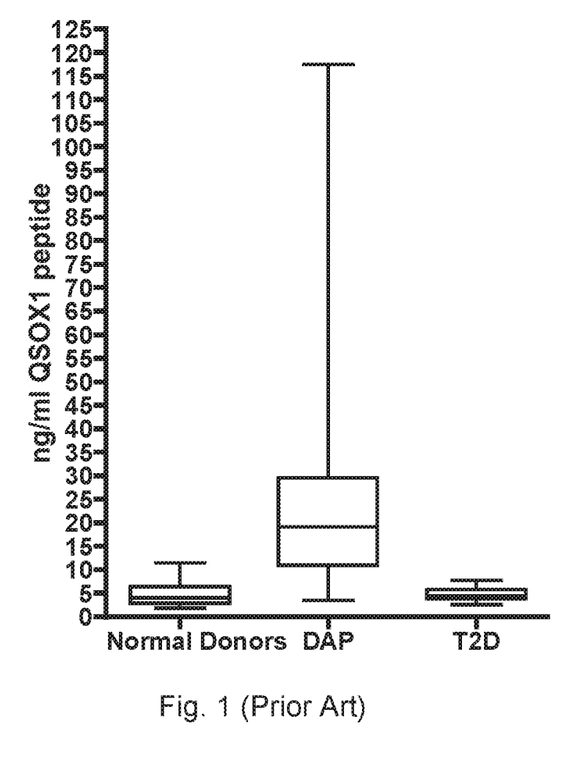
FIG. 1. QSOX1 peptide levels in plasma from 28 normal donors, 53 patients with Pancreatic Ductal Adenocarcinoma (PDA) and 8 Type 2 Diabetes patients.
Figure 2:
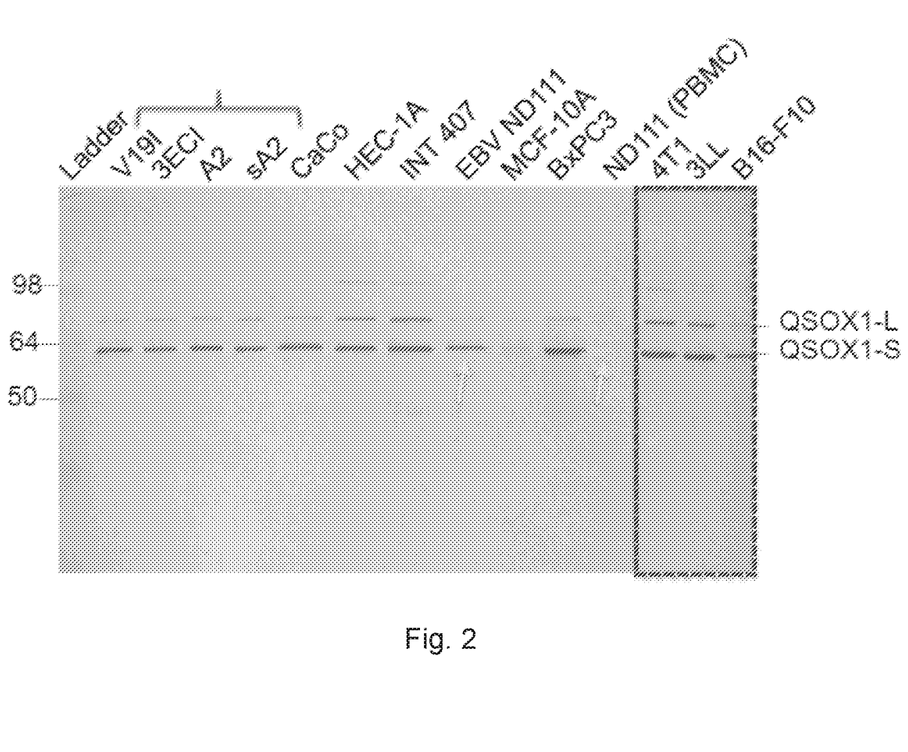
Figure 3A:
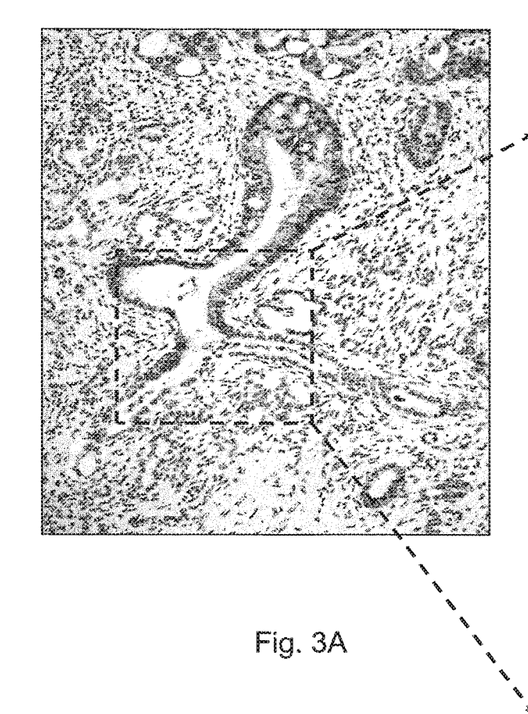
FIG. 3A. QSOX1 not expressed in adjacent stroma. Lighter edge color in the boxed area indicates QSOX1 expression.
Figure 3B:
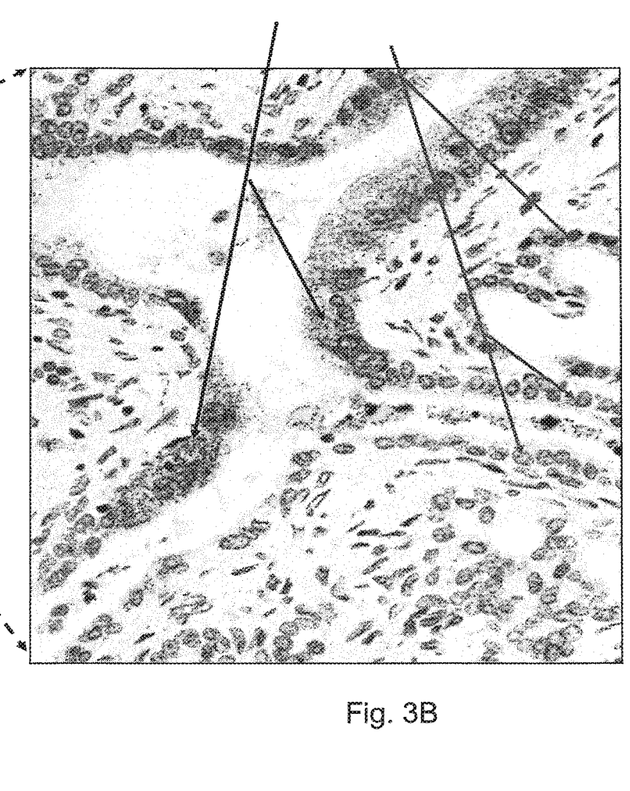
FIG. 3B. Dilated duct with dysplastic changes adjacent to invasive PanCa: QSOX1 staining highlighting pre-neoplastic cells adjacent to more normal morphology.
Figure 4A:
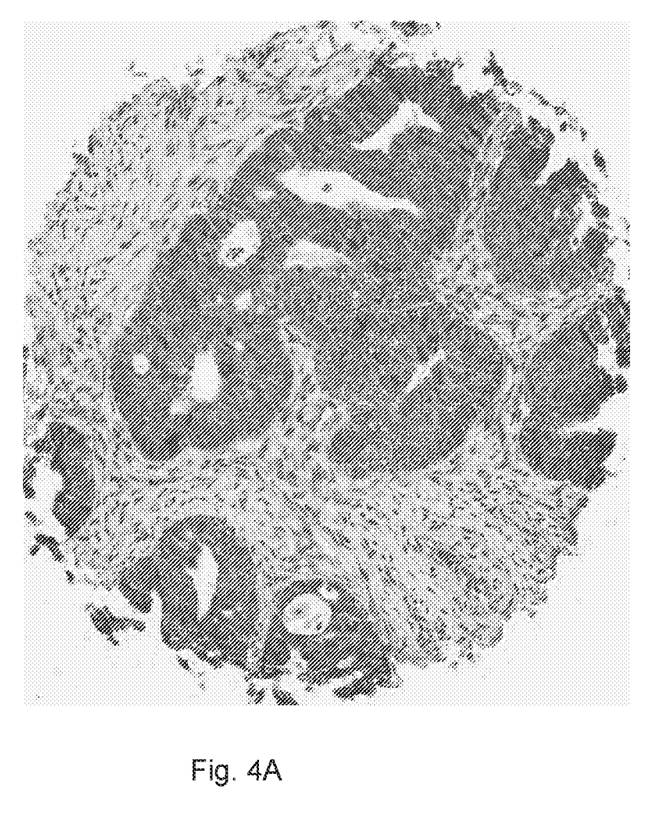
FIG. 4A. Colon Cancer. Spectrum of expression of QSOX1 (darker areas).
Figure 4B:
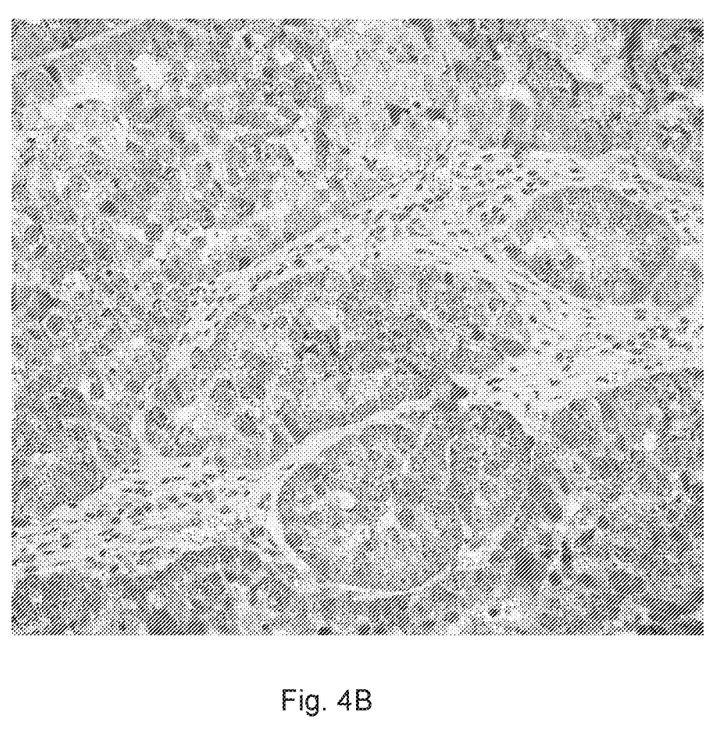
FIG. 4B. Lung Cancer. Spectrum of expression of QSOX1 (darker areas).
Figure 5A:
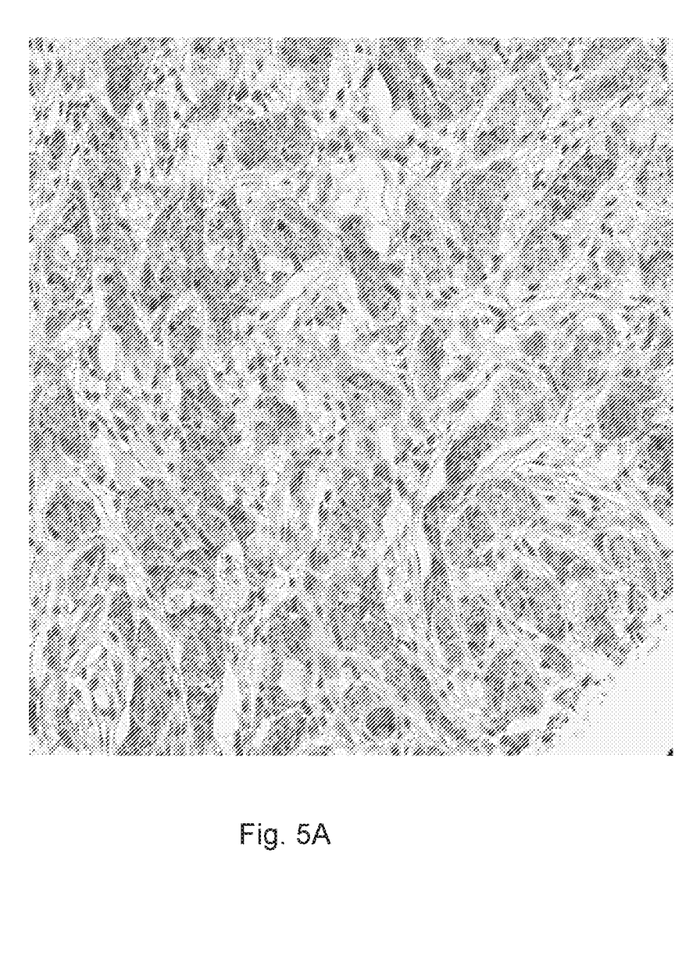
FIG. 5A. Invasive Ductal Carcinoma of the Breast. Expression of QSOX1 is shown by the darker areas.
Figure 5B:
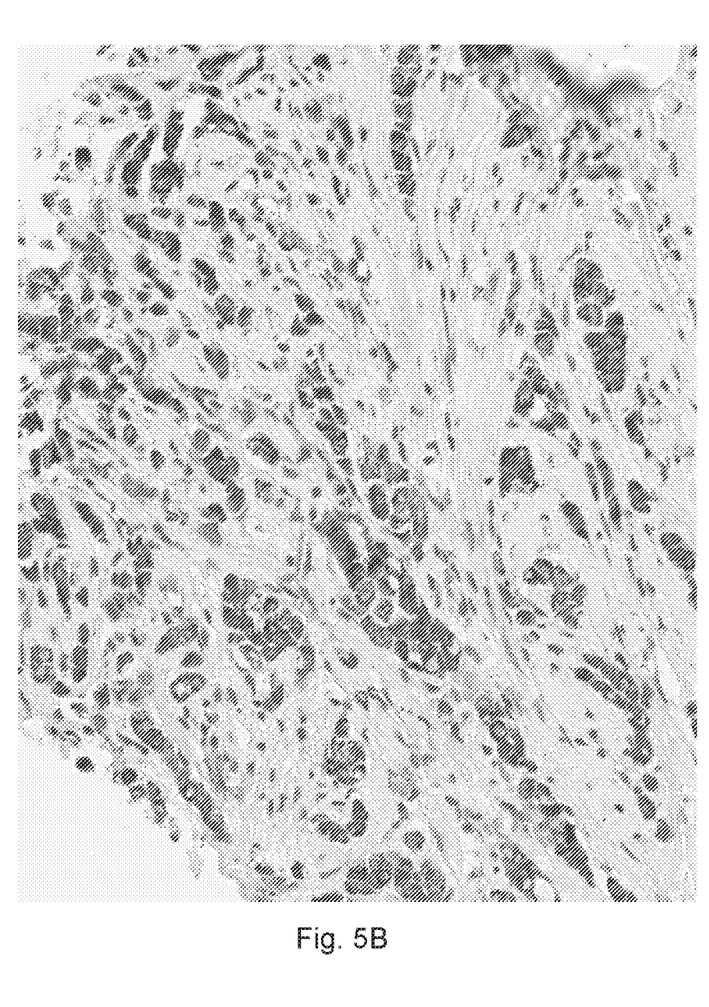
FIG. 5B. Invasive Lobular Carcinoma of the Breast. Expression of QSOX1 is shown by the darker areas.
Figure 6:
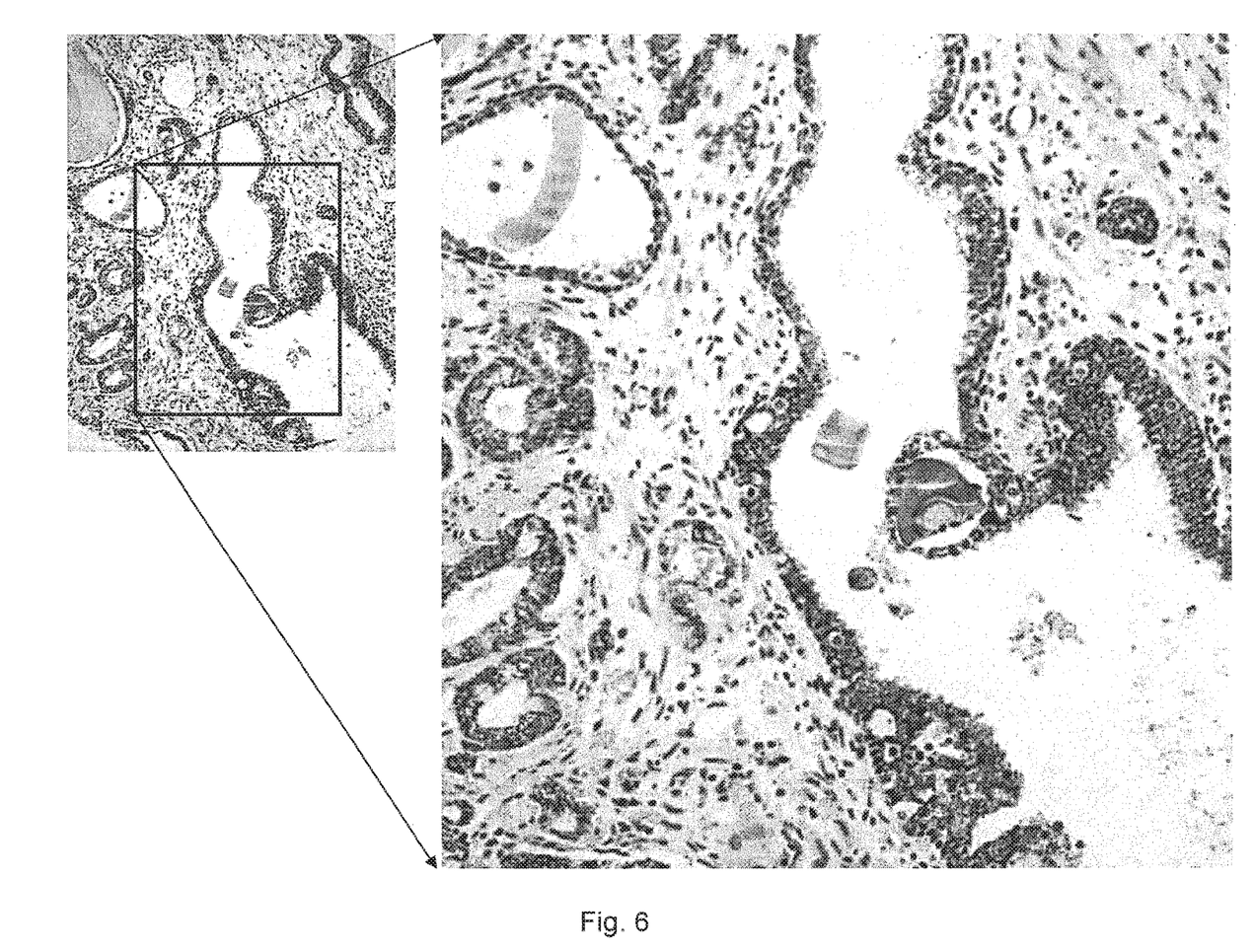
FIG. 6. QSOX1 is over-expressed in Prostate cancer (darker areas).
Figure 7:
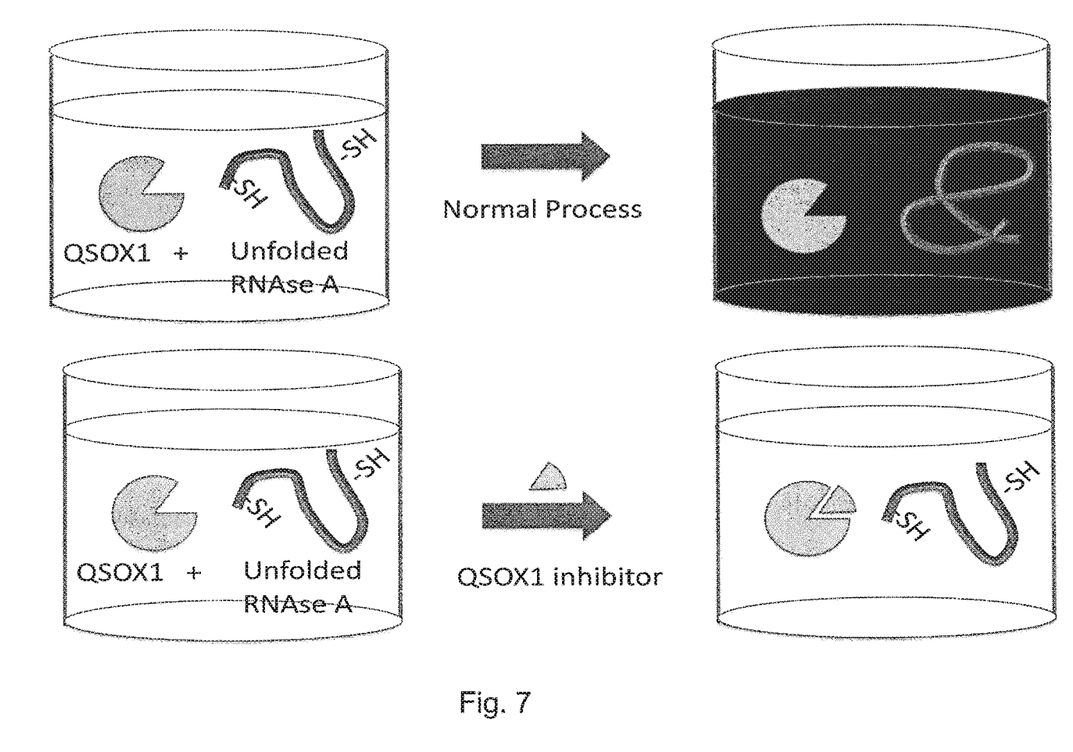
FIG. 7. An in vitro assay to screen for QSOX1 inhibitors; Fluorogenic assay (also can be HTS). Enzymatically active recombinant QSOX1 is incubated with individual compounds in individual wells of a 384 well plate. If compounds inhibit the activity of the enzyme, no $H_2O_2$ will be made by the enzyme because it can't fold RNAse A (surrogate substrate). Therefore, no fluorescence is observed. If compounds do not inhibit QSOX1, the enzyme with re-fold RNAse A, produce $H_2O_2$ and the fluorescent indicator will fluoresce.

A peptide was identified in plasma from pancreatic cancer patients that mapped back to the QSOX1 parent protein (FIG. 1, prior art). QSOX1 was shown to be over-expressed in many human and murine tumor types (FIGS. 2-6). A high throughput screening assay (HTS) was employed to screen a library of chemical compounds (50,000 compounds). The assay detects $H_2O_2$ produced by QSOX1 when it is enzymatically active (FIG. 7). Inhibition of the enzymatic activity of QSOX1 (with a chemical compound) suppresses $H_2O_2$ production, decreasing fluorescent or bioluminescent signal in the assay.

Figure 8:
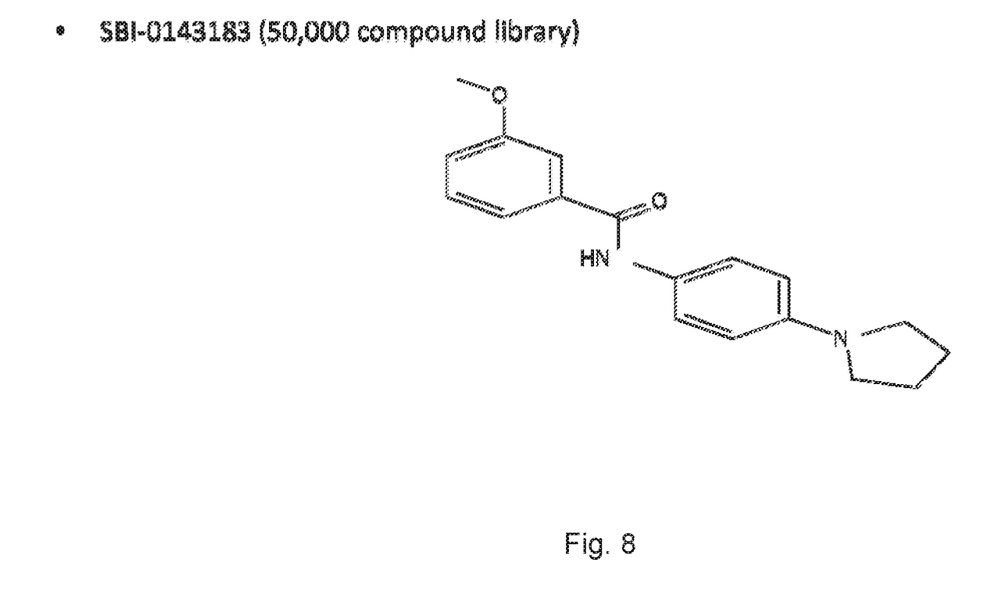
FIG. 8. High throughput screening results.
Figure 9:
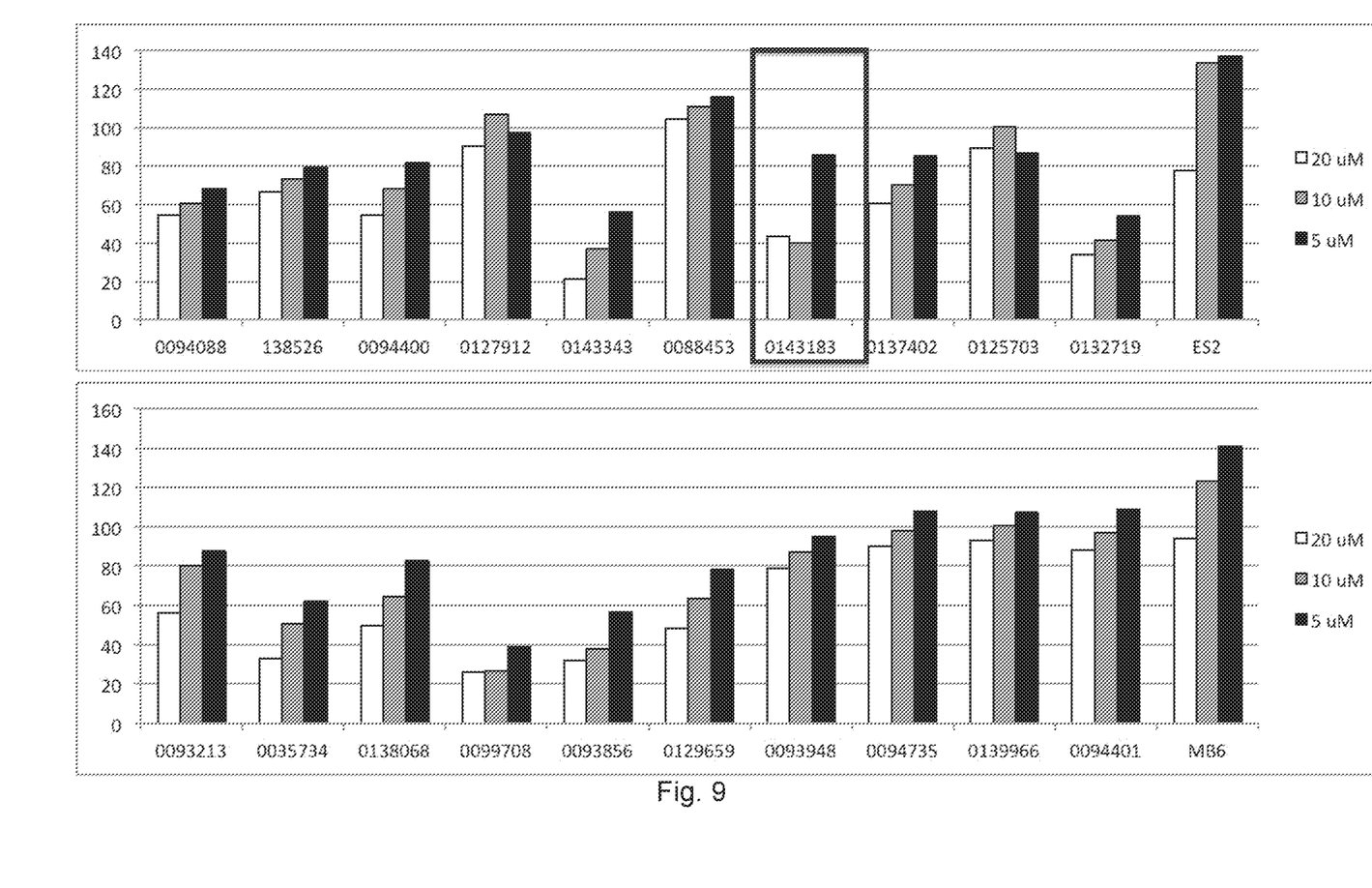
FIG. 9. Twenty lead compounds (provided by SBI from their HTS) were incubated at 3 different concentrations with MIAPaCa2 pancreatic cancer cells to determine if any of the compounds affected tumor cell viability. ES2 and MB6 are inhibitors of ALR, an enzyme similar to QSOX1.
Figure 10:
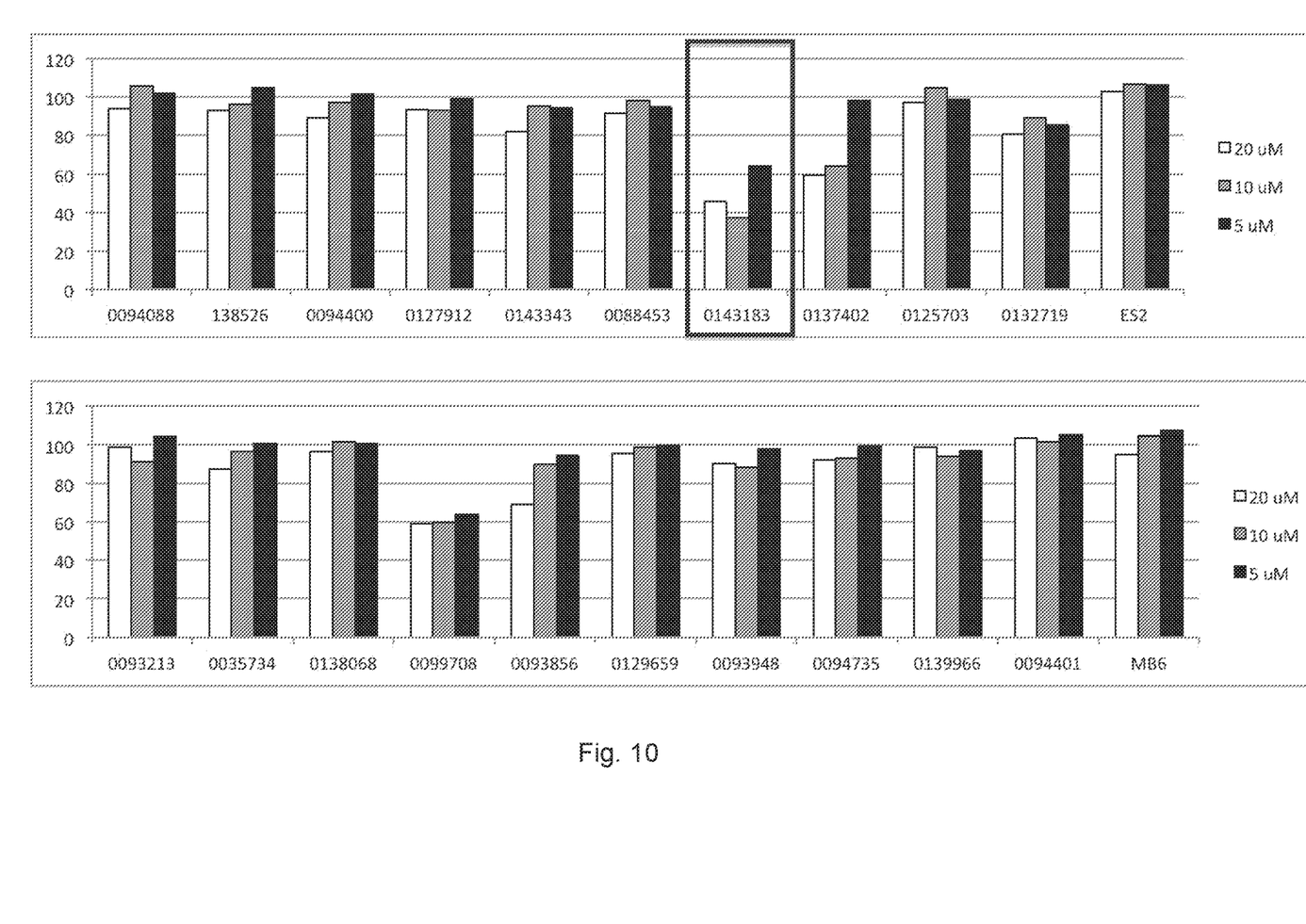
FIG. 10. Viability (MTT) assay. Twenty lead compounds (provided by SBI from their HTS) were incubated at 3 different concentrations with 786-O kidney cancer cells to determine if any of the compounds affected tumor cell viability. ES2 and MB6 are inhibitors of ALR, an enzyme similar to QSOX1. Red box shows the activity of SBI-183.

FIG. 8 shows the chemical structure of SBI-183, while FIGS. 9 and 10 demonstrate a secondary screening of 20 lead compounds identified as promising hits in HTS. The secondary screen consisted of incubating pancreatic (MIAPaCa2) and kidney (786-O) tumor cell lines with 20, 10, and 5 uM SBI-183 (0143183) for 48 hours followed by MTT assay (measure of mitochondrial respiration).

Figure 11:
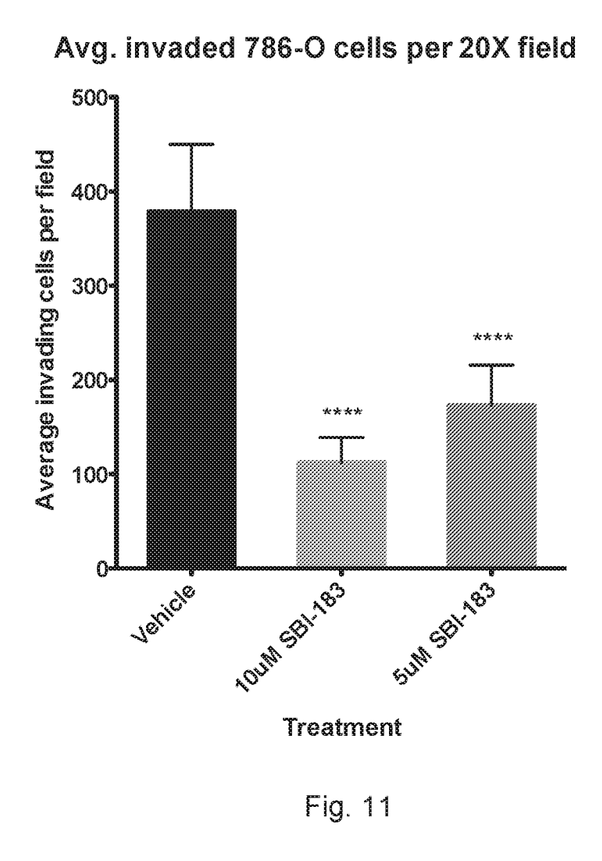
FIG. 11. Effect of Compound SBI-0143183 on Kidney cancer invasion through Matrigel (786-O). A boyden chamber experiment to determine if SBI-183 suppresses invasion of Kidney cancer cells through Matrigel.
Figure 12:
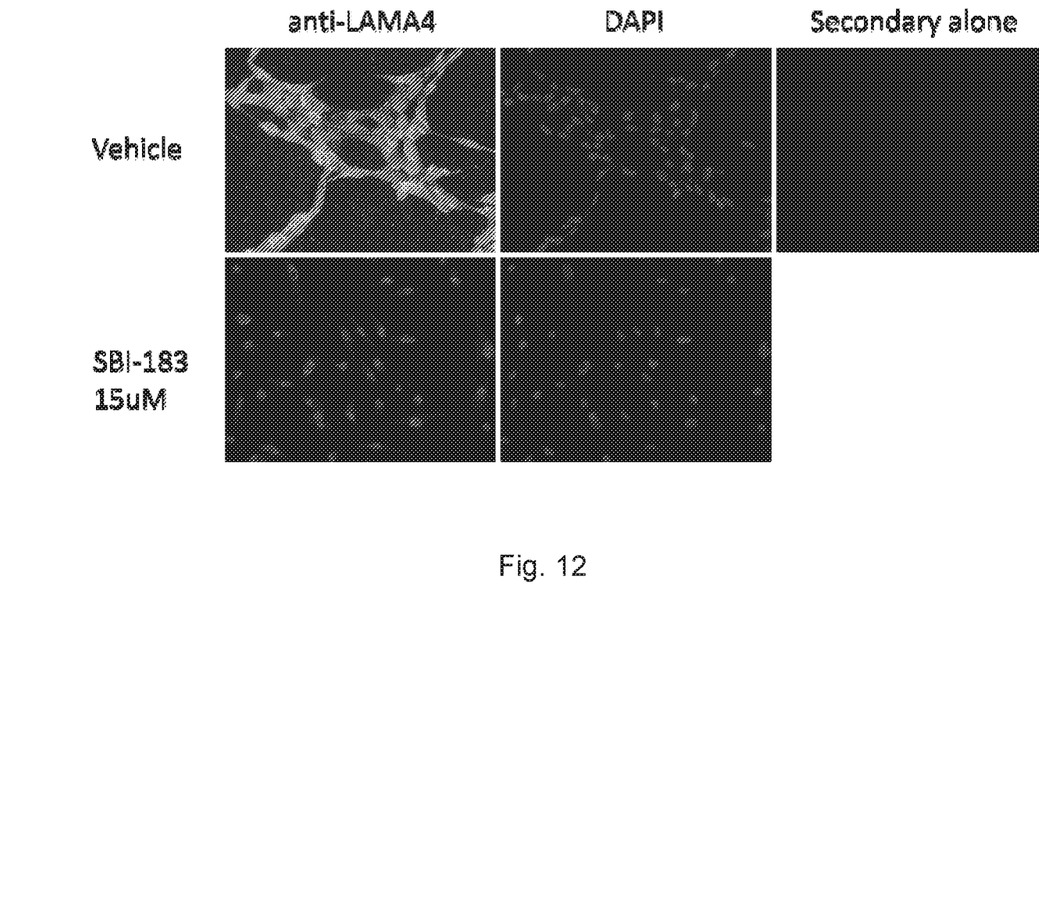
FIG. 12. 786-O Detection of laminin-α4 using anti-LAMA4 antibody in kidney cancer cells after incubation with 15 uM SBI-183. DAPI staining shows nuclei (blue). Secondary alone indicates the goat anti-mouse antibody that was used to detect binding of anti-LAMA4. This shows that lamin-4 is not deposited in the extracellular matrix of kidney cancer cells when the cells are exposed to SBI-183.
Figure 13:
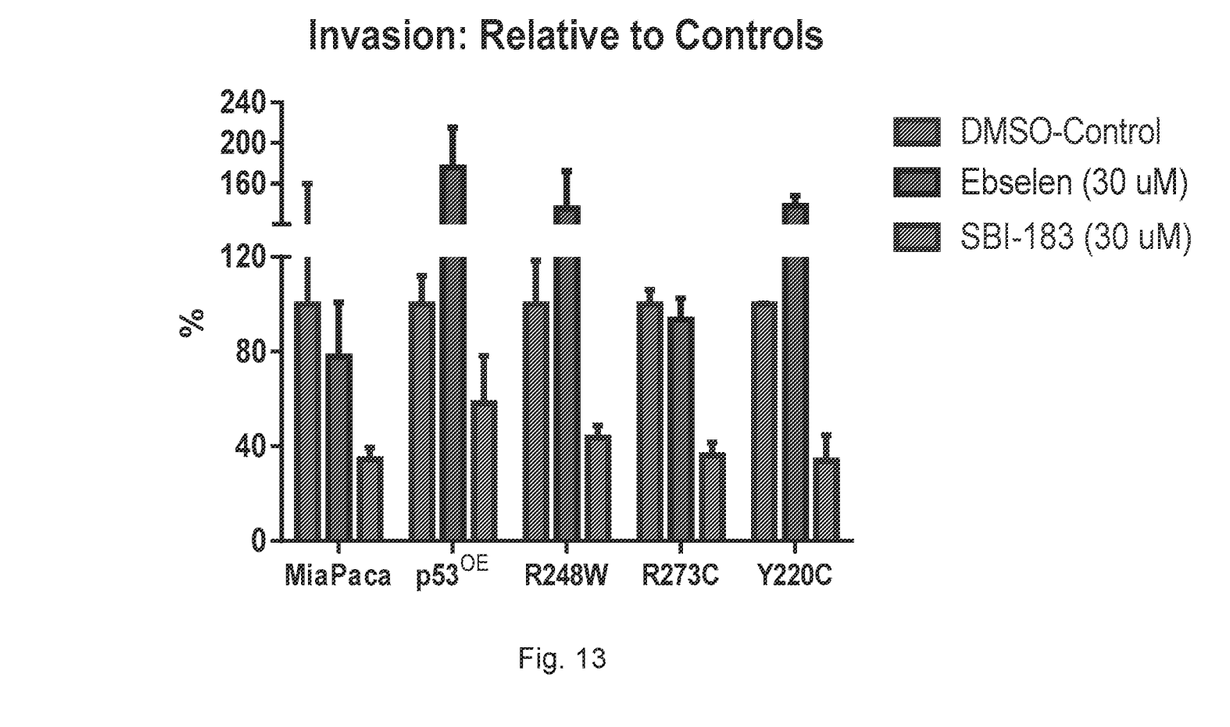
FIG. 13. SBI-183 suppresses invasion of MCF-10A-p53$^{overexpress}$ and mutant p53 breast cancer cell lines. Boyden chamber experiment to determine if SBI-183 suppresses invasion through Matrigel of MIAPaCa2 (pancreatic) and breast cancer cell lines. P53OE is MCF-10A non-malignant breast cell line containing wild type (non-mutated) p53. R248W, R273C and Y220C are three different p53 mutants expressed in MCF-10A breast cells.

FIG. 11 demonstrates that SBI-183 suppressed invasion of 786-O cells through Matrigel (in vitro surrogate for a basement membrane) in a dose-dependent manner. SBI-183 inhibits deposition of laminin-α4 into the extracellular matrix at 15 uM as shown in FIG. 12. FIG. 13 demonstrates that SBI-183 suppresses invasion through Matrigel of MIAPaCa2 pancreatic tumor cells and highly invasive MCF-10A breast cancer cell lines containing mutant p53. SBI-183 suppresses the growth of UOK117 renal cell carcinoma xenografts implanted into nude mice compared to vehicle-treated and untreated mice.

The QSOX1 enzyme is over-expressed in every histological type of tumor tested so far including blood cancers. Thus, in another embodiment, SBI-183 slows the growth and invasion of pancreatic, renal and breast cancer cells (FIGS. 11-13).

Figure 14:
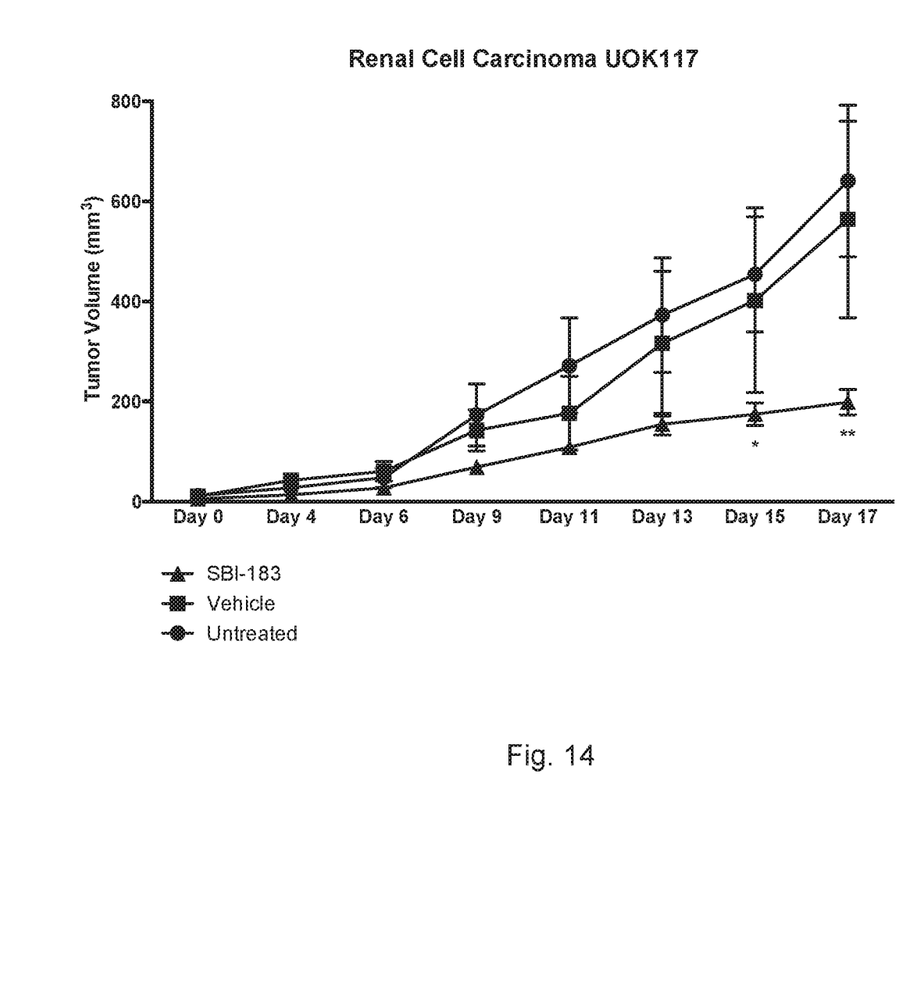
FIG. 14. SBI-183 suppresses the growth of UOK117 renal cell carcinoma xenografts in nude mice. Mice were inoculated with 1 million tumor cells in the hind flank. Treatment was started on day 7 by oral lavage at 20 mg/kg/day.

In further embodiments, SBI-183 has been tested in-vivo in a murine model of cancer. SBI-183 suppresses the growth of UOK117 renal cell carcinoma xenografts in nude mice (FIG. 14).

Figure 15:
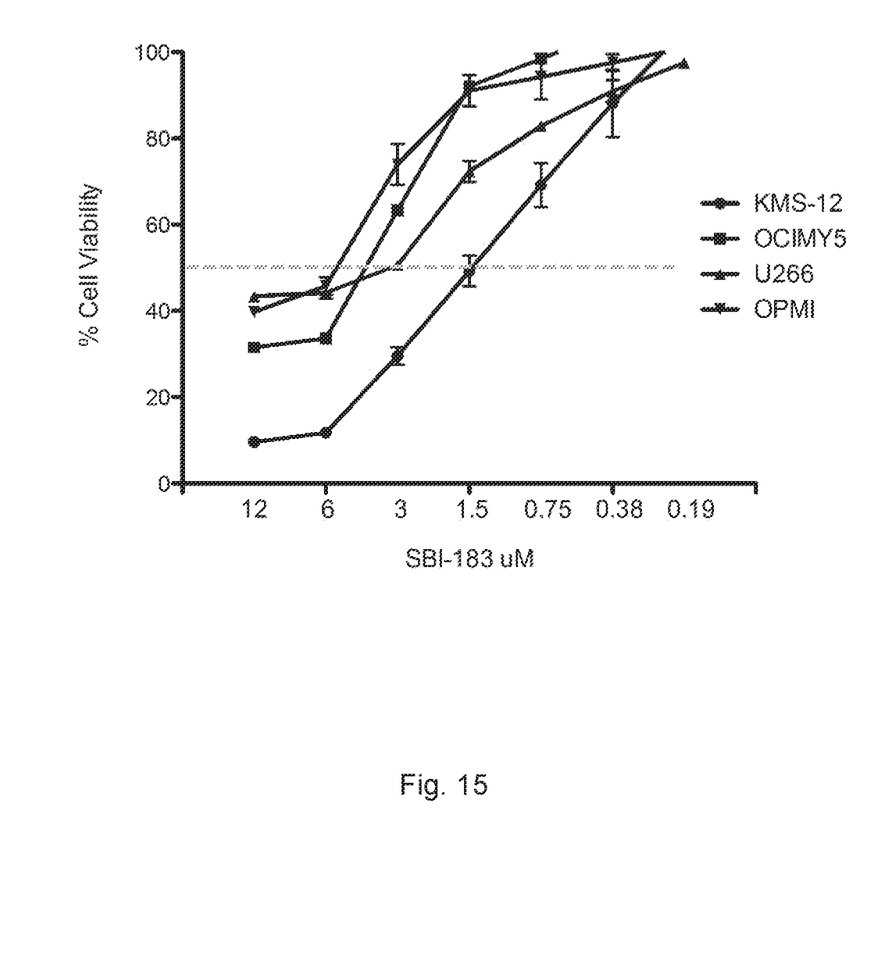
FIG. 15. MTT assay results from exposure of myeloma cell lines to SBI-183. Assay conditions: 25,000 cells per well were plated in a 96-well flat-bottom plate. 2-fold serial dilutions of SBI-183 were added to each well. % cell viability was calculated using the following formula: cmpd+cells/vehicle+cells*100%.

Moreover, MTT assay results from exposure of myeloma cell lines to SBI-183 shows decreased viability at higher does (FIG. 15). Taken together, the results disclosed herein indicate that the use of SBI-183 and related compounds inhibit neoplastic cells that over-express the QSOX1 enzyme, such as in, for example, myeloma and pancreatic, renal, and breast cancer.

SBI-183 is believed to be first-in-class, as no sulfhydryl oxidase inhibitors appear to exist in the scientific literature (and especially not one that inhibits tumor growth and metastasis).

In other embodiments, methods for neoplastic cell inhibition, tumor inhibition, and cancer treatment involving contacting a cell, a tumor, or a subject having cancer with an effective amount of SBI-183 or a pharmaceutically acceptable salt thereof. The subject can be any mammal, preferably a human. As used herein, the phrase "an amount effective" refers to the amount of inhibitor that provides a suitable inhibition and/or treatment effect.

As used herein, "treating tumors" means accomplishing one or more of the following: (a) reducing tumor mass; (b) slowing the increase in tumor mass; (c) reducing tumor metastases; (d) slowing the incidence of tumor metastases; (e) limiting or preventing development of symptoms characteristic of cancer; (f) inhibiting worsening of symptoms characteristic of cancer; (g) limiting or preventing recurrence of symptoms characteristic of cancer in subjects that were previously symptomatic; (i) increasing subject survival time; and (j) limiting or reducing morbidity of therapy by enhancing current therapies, permitting decreased dose of current standard of care therapies.

The methods of the invention can be used to treat any suitable tumor type. In one preferred embodiment, the methods are used to treat any tumor type that over-expresses QSOX1. Expression of QSOX1 can be assessed by any suitable method, including but not limited to immunohistochemistry of suitable tissue sample, polymerase chain reaction, or detection of QSOX1 peptides in suitable tissue.

In various non-limiting embodiments, techniques that can be used in the analysis include mass spectrometry (MS), two dimensional gel electrophoresis, Western blotting, immunofluorescence, ELISAs, antigen capture assays (including dipstick antigen capture assays) and mass spec immunoassay (MSIA).

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

All embodiments of any aspect of the invention can be used in combination, unless the context clearly dictates otherwise.

Non-limiting tumor types that can be treated using the methods of the invention include pancreatic, kidney, and breast. In a preferred embodiment, the tumor is a pancreatic tumor, such as a pancreatic adenocarcinoma or a neuroendocrine tumor. In a further preferred embodiment, the tumor comprises a pancreatic adenocarcinoma.

The inhibitors for QSOX1 as disclosed herein can be administered via any suitable technique or formulation, including but not limited to lipid, virus, polymer, or any other physical, chemical or biological agent, but are generally administered as part of a pharmaceutical composition together with a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be via physical injection with a needle to, for example, a tumor in the subject; topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The inhibitor described herein can also be formulated in combination with one or more additional active ingredients as desired.

In another embodiment, methods are provided for limiting tumor metastasis, comprising contacting a subject having a tumor with an amount effective of an inhibitor of QSOX1 activity, or pharmaceutically acceptable salt thereof, to limit metastasis of the tumor in the subject.

The claims are not intended to be limited to the materials, methods, embodiments and examples described herein.

What is claimed is:

1. A pharmaceutical composition, comprising:

(a)

(SBI-183)

or a pharmaceutically acceptable salt thereof; and (b) a pharmaceutically acceptable carrier.

2. A method for cancer treatment, comprising administering to a subject having a tumor an effective amount of compound SBI-183:

or a pharmaceutically acceptable salt thereof, wherein said cancer is selected from a cancer of the breast, a cancer of the pancreas, a cancer of the kidney, and myeloma.

3. The method of claim 2, wherein said cancer is a cancer of the breast.

4. The method of claim 2, wherein said cancer is a cancer of the pancreas.

5. The method of claim 2, wherein said cancer is a cancer of the kidney.

6. The method of claim 2, wherein said cancer is myeloma.

* * * * *